US010016350B2

(12) United States Patent
Pohlmann et al.

(10) Patent No.: US 10,016,350 B2
(45) Date of Patent: *Jul. 10, 2018

(54) NANOPARTICLE SYSTEM COMPRISING OIL AND UV FILTER

(71) Applicants: BIOLAB SANUS FARMACÊUTICA LTDA., Taboão da Serra-Sp (BR); UNIVERSIDADE FEDERAL DO RIO GRANDE DO SUL—UFRGS, Porto Alegre-RS (BR)

(72) Inventors: Adriana Raffin Pohlmann, Porto Alegre-RS (BR); Silvia Stanisçuaski Guterres, Porto Alegre-RS (BR); Alessandro Jäger, Porto Alegre-RS (BR)

(73) Assignees: BIOLAB SANUS FARMACÊUTICA LTDA, Taboão da Serra (BR); UNIVERSIDADE FEDERAL DO RIO GRANDE DO SUL-UFRGS, Porto Alegre (BR)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,012

(22) Filed: May 12, 2016

(65) Prior Publication Data

US 2016/0256372 A1    Sep. 8, 2016

Related U.S. Application Data

(62) Division of application No. 13/123,451, filed as application No. PCT/BR2009/000315 on Oct. 9, 2009.

(30) Foreign Application Priority Data

Oct. 10, 2008    (BR) ........................................ 080584

(51) Int. Cl.
| | |
|---|---|
| *A61K 8/40* | (2006.01) |
| *A61K 8/11* | (2006.01) |
| *A61K 8/35* | (2006.01) |
| *A61K 8/85* | (2006.01) |
| *A61K 8/92* | (2006.01) |
| *A61Q 17/04* | (2006.01) |
| *A61K 8/49* | (2006.01) |
| *A61K 8/84* | (2006.01) |

(52) U.S. Cl.
CPC ................. *A61K 8/40* (2013.01); *A61K 8/11* (2013.01); *A61K 8/35* (2013.01); *A61K 8/4973* (2013.01); *A61K 8/84* (2013.01); *A61K 8/85* (2013.01); *A61K 8/922* (2013.01); *A61Q 17/04* (2013.01); *A61K 2800/412* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 6,203,802 B1 | 3/2001 | Handjani et al. | |
| 6,436,375 B1 | 8/2002 | Lapidot et al. | |
| 7,001,592 B1* | 2/2006 | Traynor | ................. A61K 8/042 424/400 |
| 2005/0175651 A1* | 8/2005 | Simonnet | ............. A61K 9/5146 424/401 |

FOREIGN PATENT DOCUMENTS

| | | |
|---|---|---|
| BR | 0303404-6 A | 8/2005 |
| EP | 1834635 A1 | 9/2007 |
| JP | 2000-319120 A | 11/2000 |
| WO | WO 93/05753 A1 | 4/1993 |
| WO | WO 2008/072239 A2 | 6/2008 |
| WO | WO 2009/007264 A2 | 1/2009 |

OTHER PUBLICATIONS

Zanatta et al. (Low cytotoxicity of creams and lotions formulated with buriti oil (Mauritia flexuosa) assessed by the neutral red release test, Food and Chemical Toxicology, 2008, p. 2776-2781, published May 13, 2008).*
Albuquerque, M.L. et al. "Characterization of Buriti (Mauritia flexuosa L.) Oil by Absorption and Emission Spectroscopies". J. Braz. Chem. Soc. 2005, vol. 16, No. 6A, pp. 1113-1117.
Avobenzone MSDS.
Bouchemal et al, Nano-emulsion formulation using spantaneous emulsification: solvent, oil and surfactant, Int. J. Pharm., 2004, vol. 280, pp. 241-251.
Croda product monograph, 2004.
Fessi, H. et al. "Nanocapsule formation by interfacial polymer deposition following solvent displacement". International Journal of Pharmaceutics, 1989, vol. 55, pp. R1-R4.
Fessie et at., "Spray-drying nanocapsules in the presence of collodal silica as dying auxiliary agent: formulation and process variable optimization using experimental design," Pharm. Res. 2007, vol. 24, pp. 650-661.
Flor, J. et al. "Protetores Solares". Quim. Nova, 2007, vol. 30, No. 1, pp. 153-158.
Forestier, "Rationale for sunscreen development," J. Am. Acad Dermatol., 2008, vol. 58, S133-137.
Galindo-Rodriguez, S. et al. "Physicochemical Parameters Associated with Nanoparticle Formation in the Salting-out, Emulsification-Diffusion, and Nanoprecipitation Methods". Pharmaceutical Research, Aug. 2004, vol. 21, No. 8, pp. 1428-1439.

(Continued)

*Primary Examiner* — Bethany P Barham
*Assistant Examiner* — Ping Cao
(74) *Attorney, Agent, or Firm* — Arent Fox LLP

(57) ABSTRACT

The present invention describes cosmetic nanotechnology, comprising polymeric nanoparticles containing oil and UV filter, photoprotective compositions comprising polymeric nanoparticles described herein, methods of prevention of diseases of the skin, and processes for the preparation of the polymeric nanoparticles described herein.

6 Claims, 5 Drawing Sheets

(56) References Cited

OTHER PUBLICATIONS

Guterras et al, "Polymeric nanoparticles, nanospheres and nanocapsules for cutaneous applications," Drugtarget, 2007, vol. 2, pp. 147-157.
Haag, M.C. et al. "Produção não-madeireira e desenvolvimento Sustentável na Amazônia". Brasilia, Janeiro, 2005, 52 pgs.
Maria, V. et al. "Como as empresas brasileiras de cosméticos estão utilizando o conhecimento tradicional e as plantas medicinais". Dec. 2004, 9 pgs.
Meirelles et al., "Densities and viscosities of vegetable oils and nutritional values," J Chem. Eng. Data, 2008, vol. 53, pp. 1846-1853.
Ribeiro, R.P. et al. "Avaliaçã do Fator de Proteção Solar (FPS) in vitro de produtos comerciais e em fase de desenvolvimento". pp. 85-88.
Schaffazick, S.R. et al. "Caracterização E Estabilidade Fisico-Quimica de Sistemas Poliméricos Nanoparticulados Para Administração de Fármacos". Quim. Nova, 2003, vol. 26, No. 5, pp. 726-737.
Wu et al., "Nanotechnology in Cosmetics: A Review," Cosmetics & Toiletries, Apr. 1, 2012, pp. 1-5.
"Speciality ingredients for personal care," Croda Chemicals Europe Ltd., Nov. 2005, 2nd edition, pp. 1-60.

\* cited by examiner

Graph A NANO

Graph B REFERENCE

NANOPARTICLE SYSTEM COMPRISING OIL AND UV FILTER

CROSS-REFERENCE TO RELATED APPLICATIONS

This application is a Divisional of U.S. patent application Ser. No. 13/123,451, filed Jul. 15, 2011, which is a National Stage entry of International Application No. PCT/BR2009/000315, filed Oct. 9, 2009, which claims priority to Brazilian Patent Application No. PI0805854-7, filed Oct. 10, 2008. The disclosures of the prior applications are hereby incorporated in their entirety by reference.

FIELD OF THE INVENTION

The present invention describes cosmetic nanotechnology, comprising nanoparticles containing oil and UV filter, photoprotective compositions comprising the same and methods of prevention of diseases of the skin.

BACKGROUND OF THE INVENTION

The solar spectrum that reaches land surface is formed predominantly by ultraviolet (100 to 400 nm), visible (400 to 800 nm) and infrared (above 800 nm) radiations. Ultraviolet radiation (UV) is responsible for the activation of photochemical reactions. The effect of solar radiation on man depends on the individual characteristics of the exposed skin, the intensity of the radiation, and the frequency and time of exposure of the skin to radiation. (Flor, J., et al., "Protetores Solares" Quimica Nova, v. 30, 2007).

The band of UV radiation can be divided in three parts: UVA (320 to 400 nm), UVB (280 to 320 nm) and UVC (100 to 280 nm) (Flor, J., et al., 2007).

UVA radiation penetrates the dermis and induces the pigmentation of skin, promoting bronzing by means of augmenting the synthesis of melanin. Histologically, UVA radiation also can cause damage to the peripheral vascular system, induce cancer of skin, and in an indirect manner promote formation of free radicals. (Flor, J., et. al., 2007). Over time, it provokes alterations in collagen and elastic fibers, leading to premature aging (Ribeiro, R. P., et al., "Avaliação do Fator de Proteção Solar (FPS) in vitro de produtos comerciais e em fase de desenvolvimento" Revista Infarma, v. 16, 2004).

UVB radiation can promote sunburns (erythemas), bronzing of the skin, and premature aging. UVB radiation is also responsible for the transformation of skin ergosterol to vitamin D. Frequent and intense exposure to UVB radiation can cause breaks in DNA, and suppress the immune response of the skin. In this way, beyond increasing the risk of fatal mutations, manifested in the form of skin cancer, its activity reduces the chance of a malignant cell being recognized and destroyed by the organism (Flor, J., et al., 2007).

The deleterious effects of UV radiation in man can be minimized by the use of UV filters, frequently utilized in cosmetic and dermatological compositions (Flor, et. al., 2007). Currently, UV filters have been developed to provide protection in the bands of UVA and UVB.

There are two classes of UV filters: organic and inorganic, routinely and respectively classified as filters that absorb radiation (chemical filters) and filters that reflect radiation (physical filters). A second and simpler classification is based on organic filters having organic compounds, and inorganic filters having metal oxides.

A study carried out by the American organization EWG (Environmental Working Group), demonstrated that 84% of the tested photoprotective formulations offered inadequate protection to UV radiation. In this sense and the need for preparations with greater efficacy for example, better efficiency in protection and greater chemical stability—the segment has demanded from large manufacturers to perfect new UV filters (Flor, J., et al., 2007).

To avail a UV filter to the consumer, it is necessary that it incorporates a second ingredient, for example, an excipient. This association of UV filter/second ingredient is denominated a sunscreen or photoprotective composition. Some characteristics are desired so that the sunscreens can be commercialized. Beyond chemistry, photochemistry and thermically inertness the protectors must exhibit other characteristics, as for example, to be nontoxic, not to be sensitizing, irritating or mutagenic, not to be volatile, possess appropriate characteristics of solubility, not to be absorbed by the skin, not to change color, not to stain skin and clothes, to be colorless, to be compatible with formulation and conditioning material and be stable in the final product (Flor, J., et al., 2007).

The preparation of a sunscreen in general has two basic components: active ingredients (organic and/or inorganic filters) and inactive ingredients (for example, excipients). The mixture of inactive ingredients defines the type of vehicle. Various vehicles can be utilized in the preparation of sunscreens, from simple solutions to structures more complex as emulsions (Flor, J., et. al., 2007).

Various methods are related in the literature for the preparation of nanoparticles, which can be classified as: 1) methods based on the in situ polymerization of dispersed monomers; or 2) methods based on the precipitation of pre-formed polymers (Schaffazick, S. R., et al., 2003). The principal the precipitation methods are salting-out (Galindo-Rodriguez, S., et al., "*Physicochemical parameters associated with nanoparticle formation in the salting-out, emulsification-diffusion, and nanoprecipitation methods*" *Pharmaceutical Research,* 21, 1428-1439, 2004), emulsification-diffusion (Leroux, J. C., et al., "*New approach will be the preparation of nanoparticles by an emulsification-diffusion method*" European Journal of Pharmaceutics and Biopharmaceutics, 41, 14-18, 1995), nanoprecipitation and interfacial polymer deposition (Fessi, H., et al., "*Nanocapsules formation by interfacial polymer deposition following solvent displacement*" International Journal of Pharmaceutics, 55, R1-R4, 1989).

The cosmetic and cosmeceutical industries also have utilized substances coming from flora: phytocosmetics and phytocosmeceuticals. In this sense, with regard to biodiversity, Brazil relies on important ecosystems, including Amazonian, as arsenals of plants with proven or potential uses for the cosmetic industry (Marinho, V. M. C., 2004).

Among these plants include, without limitations, crabwood (andiroba or *Carapa guianensis*), buriti (*Mauritia flexuosa* and *Mauritia vinifera*), cacao (*Theobroma cacao*), German chamomile (*Matricaria recutita, Matricaria chamomilla* and *Matricaria suaveolens*), brazilnut (*Bertholletia excelsa*), theobroma (*Theobroma grandiflorum*), guarana (*Paullinia cupana*), macela (*Achyrccline satureioides*), passion fruit (*Passiflora edulis*), mate (*Ilex paraguariensis*), Surinam Cherry (*Eugenia uniflora*), murumuru palm (*Astrocaryum murumuru*), batua palm (*Oenocarpus batua*), tucuma (*Astrocaryum tucuma*), coconut (*Cocos nucifera* L.), peanut (*Arachis hypogaea*), cotton (*Gossypium* L.), sesame (*Sesamum indicum*) and coffee (*Coffea arabica*), and others.

The pulp of buriti (also known as muriti, and scientific names *Mauritia flexuosa* and *Mauritia vinifera*) is basically constituted of fatty acids, tocopherols and carotenoids. After the extraction of the pulp, the composition of the buriti oil presents good stability for long periods of time (Albuquerque, M. L. S., et al., *"Characterization of Buriti (Mauritia flexuosa L.) Oil by Absorption and Emission Spectroscopies" J. Braz. Chem. Soc., Vol.* 16, No. 6A, 1113-1117, 2005; Pastore Jr., F., et al., "Introdução à Produção de Cosméticos—Uma abordagem teórica e prática com utilização de produtos da flora amazônica" UNE, January 2005).

Japanese patent application 2000319120 describes a cosmetic composition that contains one or more vegetable extracts (among them, extract of buriti) and exhibits properties of prolonged humidity retention of the skin, providing prevention or reduction of diseases of the skin, as, for example, dryness and cracks.

Brazilian patent application PI 0303404-6 contemplates the use of buriti oil in the preparation of cosmetic formulations, as a potentiator of solar protection and source of emollients and antioxidants.

SUMMARY OF THE INVENTION

The present invention describes a nanoparticle comprising oil and UV filter that are co-encapsulated. The nanoparticle can be a polymeric nanoparticle, a nanocapsule, or a polymeric nanocapsule. The nanoparticies can also contain surfactants, pharmaceuticals, active cosmetic compounds, UV filter stabilizers, enzymes and/or mixtures thereof.

In some aspects, the disclosure provides a photoprotective composition that includes the nanoparticle described herein, in combination with one or more physiologically acceptable excipients. In another aspect, the disclosure provides a photoprotective composition that includes the nanoparticle described herein, in combination with one or more cosmetic auxiliaries, for example, UV filters, fragrances, antibacterial agents, insect repellents, vitamins, antioxidants, emollients, buffers, preservatives, coloring, emulsifiers, thickening agents, UV filter stabilizers, and combinations thereof.

In some aspects, the disclosure provides a use of the nanoparticles described herein in the preparation of a photoprotective composition.

In some aspects, the disclosure provides a method of preventing diseases of the skin, including disorders of the skin. One method of preventing diseases, for example, includes administration of the photoprotective composition described herein on the skin of the individual.

The present invention also describes processes for the preparation of the nanoparticles described herein and the photoprotective composition.

DETAILED DESCRIPTION OF THE INVENTION

Figure 1:
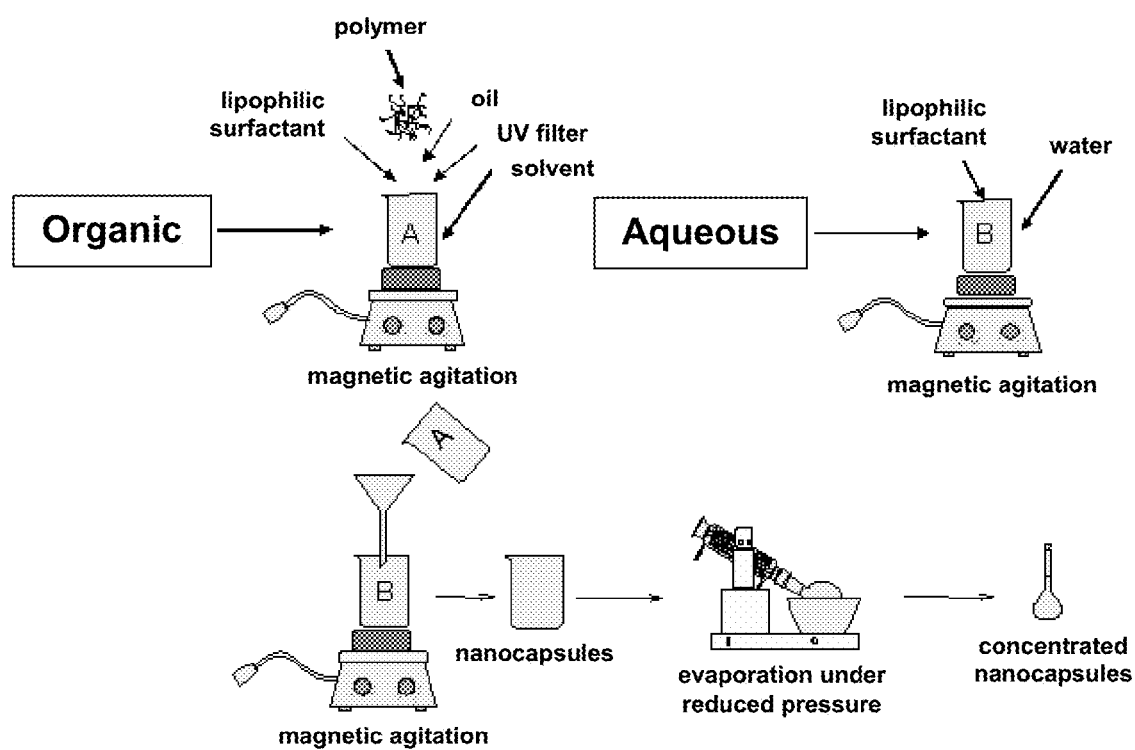
FIG. 1 presents a schematic of the method of interferential deposition, for the obtainment of nanocapsules.

The present invention describes nanoparticles comprising encapsulated oil and UV filter. The nanoparticle can be a polymeric nanoparticle, a nanocapsule, or a polymeric nanocapsule.

The nanoparticles described herein include nanocapsules with (i) a particle size from about 1 nm to about 1000 nm, (II) a polydispersion index from about 0.001 to about 0.700, and (III) a zeta potential in modulus from about −100 mV to about +100 mV; and preferentially, nanocapsules with a mean diameter of about 250 nm, a polydispersion below about 0.4, and a zeta potential about −10 mV.

The oil described herein can include mineral oil, vegetable oil, synthetic oil, or a combination thereof. Examples of mineral oil include aliphatic (saturated or unsaturated), aromatic, cyclic, or acyclic hydrocarbons. Examples of synthetic oil include medium chain triglycerides, triacylglycerols and derivatives thereof, and fatty acid esters from high molecular weight alcohol. Examples of vegetable oil include fixed oils and essential oils, which optionally can have photoprotective activity and/or potentiate photoprotective activity.

Preferentially, the oil included in the nanoparticies is vegetable oil, and more preferentially, buriti oil, which can be used in a range of about 0.001% to about 50% of the total weight, and preferentially present in about 3% of the suspension.

The UV filters included in the nanoparticles can be an organic filter, inorganic filter, or a combination thereof, which can be used in a range of about 0.001% to about 50% of the total weight, and preferentially present in about 0.1% to about 1.0%. More preferentially, a combination of inorganic filter and organic filter can be used.

Examples of organic UV filters include, but are not limited to, octocrylene, avobenzone, oxybenzone (benzophenone-3), Tinosorb® S (bemotrizin 1), octyl-p-methoxycinnamate, octyl salicylate, Eusolex® 6300 (methylbenzyidene camphor), Tinosorb® M (bisoctrizole), octyl triazone, cinoxate, octyl methoxycinnamate, Padimate® O, phenylbenzimidazole sulfonic acid, sulisobenzone, TEA-salicylate, oxybenzone, dioxybenzone, ethylhexyl methoxycinnamate, aminobenzoic acid, digalloyl trioleate, diethanolamine methoxycinnamate, ethyl-4-bis(hydroxypropyl)aminobenzoate, 2-ethylhexyl 2-cyano-3,3-diphenylacrylate, homosalate, glyceryl aminobenzoate, methyl anthranilate, ethylhexyl salicylate, Padimatee A, ethylhexyl methoxycinnamate (Uvinul® MC 80), and combinations thereof. More preferentially, the organic filter octocrylene and avobenzone can be used.

Examples of inorganic UV filters include, but are not limited to, zinc oxide, titanium dioxide, colloidal silicon dioxide and derivatives thereof. More preferentially, the inorganic filter titanium dioxide can be used.

Examples of polymer coatings include, but are not limited to, natural or synthetic, biodegradable and/or biocompatible polymers, as, for example, synthetic aliphatic polyesters, PCL, PLA, PGA, PLGA and diblocks PCL-b-PEG, PLA-PEG, and others, the acrylic derivatives (poly(alkyl methacrylate), poly(alkyl acrylate), poly(methacrylic acid) and copolymers thereof, poly-acrylamides and poly-methacrylamide, poly-alkyl cyanoacrylates) or polyurethanes and polysaccharides, as for example chitosan and cellulose derivatives can be used separately or in mixtures in the range of about 0.0001% to about 50% of the total weight, preferentially present at about 1.

Examples of synthetic polymers include, but are not limited to, polystyrene, polyesters, polyphosphazenes, polyethylene glycol (PEG), polyvinyl alcohol (PVA), polyacrylamides, polyacrylates, polyvinyl pyrrolidinones (PVP), polyallylamines and copolymers thereof, polyethylenes, polyacrylics, polymethacrylates, polyanhydrides, polysiloxanes, polyoxyethylenes and copolymers thereof, and/or derivatives thereof and/or copolymers thereof.

Examples of synthetic aliphatic polyesters include, but are not limited to, poly(ε-caprolactone) (PCL), poly(glycolic acid) (PGA), poly(lactic acid) (PLA), poly(lactic-co-glycolic acid) (PLGA), poly(hydroxybutyric acid) (PHB) and poly (hydroxyvaleric acid) (PHV), poly(cyanoacrylates), poly(methylidene malonate), and copolymers thereof. More preferentially, the poly(ε-caprolactone) (PCL), can be used.

Examples of polymethacrylates include, but are not limited to, Eudragit®.

The nanoparticle can contain surfactants, antioxidants, vitamins, preservatives, colorings, pharmaceuticals, active cosmetic compounds, UV filter stabilizers, enzymes, repellents, tensors, emollients and/or mixtures thereof, contained in the core of the nanoparticle and/or in the coating of the nanoparticle.

Examples of surfactants include, but are not limited to, castor oil ethoxylate, Pluronic F68, Steareth (Brij), Tween 20 (Polysorbate 20), Tween 40 (Polysorbate 40), Tween 60 (Polysorbate 60), Tween 80 (Polysorbate 80), sodium lauryl sulfate, Crillet 1, Crillet 4 HP, Crillet 4 NE, Cremophor RH40, Cremophor RH60, Cremophor EL, Etocas 30, Mkkol HCO-60, Labrasol, Acconon MC-8, Gelucire 50/13, Gelucire 44/14, Myrj, polyoxamers, Epikuron 170, lecithin and derivatives thereof, phospholipids and derivatives thereof, Span (sorbitan monostearate), glycerol monostearate, Capmul MCM, Capmul MCM 8, Capmul MCM 10, Imwitor 988, Imwitor 742, Imwitor 308, Labrafil M 1944 CS, Labrafil M 2125, Capryol PGMC, Capryol 90, Lauroglycol, Captex 200, fatty acid ethoxylate, Plurol oleique, Crill 1, Crill 4, Maisine, Peceole, Arlacel 9135, and mixtures thereof.

The surfactants can be present in a range of about 0.0001% to 50% of the total weight, separately or in combination.

Examples of the pharmaceuticals include, but are not limited to, anti-inflammatory drugs, antioxidants, or combinations thereof, and can be present in a range of 0% to about 50% of the total weight, separately or in combination.

Examples of anti-inflammatory drugs include, but are not limited to, alpha-bisabolol, Drieline, Sensiline, glycyrrhizinic acid and limonoid.

Examples of antioxidants include, but are not limited to, vitamin A, vitamin E, vitamin C, green tea, green coffee, soy isoflavone, Phycojuvenine, Smart vector UVCE, butylated hydroxytoluene (BHT), butylated hydroxyanisole (BHA) and/or combinations thereof.

Examples of vitamins include, but are not limited to, vitamin B, C, D, E, and K, or combinations thereof, and can be present in the range of 0% to about 50% of the total weight.

Examples of preservatives include, but are not limited to, parabens, ascorbic acid, phenoxyethanol, imidazolidinyl urea, diazolidinyl urea, sorbic acid or combinations thereof, and can be present in a range of 0% to about 10% of the total weight.

Examples of repellents include, but are not limited to, citronella, chrysanthemum, vitamin B and/or combinations thereof, and can be present in a range of 0% to about 50% of the total weight.

Examples of tensors include, but are not limited to, peptides, and can be present in a range of 0% to about 50% of the total weight.

Examples of emollients include, but are not limited to, Aloe Vera, hyaluronic acid, allantoin and/or combinations thereof, and can be present in a range of 0% to about 50% of the total weight.

The nanoparticles of the present invention can be prepared by in situ polymerization of dispersed monomers, by emulsion or interfacial polymerization, or by precipitation of pre-formed polymer, with the utilization of solvents, by nanoprecipitation, interfacial deposition, emulsification-evaporation, or emulsification-diffusion.

Examples of solvents include, but are not limited to, acetone, ethanol, water, propylene glycol, propylene carbonate, chloroform, glycerin, dichloromethane, methanol, ethyl acetate, dimethylformamide, dimethylsulfoxide, tetrahydrofuran, ketones, alcohols and halogenated derivatives.

The present invention also describes a photoprotective composition comprising the nanoparticles described herein. The nanoparticle can be a polymeric nanoparticle, a nanocapsule, or a polymeric nanocapsule. The photoprotective composition can include one or more physiologically acceptable excipients. More preferentially, the nanocapsule can be used.

The photoprotective compositions can be in a variety of forms. These include, but are not limited to, creams, lotion, hydro-alcoholic lotion, gel, oil, etc.

The photoprotective composition of the present invention can include cosmetic auxiliaries, for example, UV filters, fragrances, antibacterial agents, insect repellants, vitamins, antioxidants, emollients, buffers, preservatives, coloring, emulsifiers, thickening agents, UV filter stabilizers, and combinations thereof.

The photoprotective composition of the present invention has the following characteristics/properties:
  increase in photostability, when compared to a composition with oil and encapsulated UV filter;
  odorless or absence disagreeable odor, when compared to a composition with oil and encapsulated UV filter;
  optionally, an increase in the solar protection factor (SPF) when compared to a composition with oil and encapsulated UV filter;

In some aspects, the disclosure provides a use of the nanoparticles described herein in the preparation of photoprotective composition.

The present invention also describes a process for the preparation of the photoprotective composition described herein. Such process includes obtaining nanocapsules, with a coating comprising polymeric material and a core comprising oil and UV filter, by interfacial deposition of pre-formed polymers or nanoprecipitation, and optionally mixing said nanoparticles with one or more cosmetically acceptable auxiliaries and/or physiologically acceptable excipients.

FIG. 1 presents the principle steps of the method of interfacial polymer deposition.

In another aspect, the disclosure provides a method of preventing disease of the skin, including the administration of the photoprotective composition described herein on the skin of the individual.

The composition is preferentially administered to the individual by topical route.

Examples of diseases that can be prevented by the invention include, but are not limited to, aging, wrinkles, cutaneous cracks, dryness, oxidation, burns, erythemas, dermatosis, melasma, skin spots, dermatitis and cancer.

Illustrative examples and results are presented for the nanoparticles, and the compositions, of the present invention. The examples are intended to show and illustrate the practical realization of the invention, and are not intended to be limiting.

Example 1

1.1. Photoprotective Composition for the Body (SPF 30):

| Components | SPF 30 |
|---|---|
| PHASE A | |
| Acrylates/C10-30 alkyl acrylate crosspolymer | 0.05 |
| Triglycerides of caprylic/capric Acid | 2.0 |
| Dimethicone | 2.0 |
| Isostearyl alcohol (and) butylene glycol cocoate (and) ethylcellulose | 4.5 |
| Ceteareth-20 | 1.0 |
| PEG-30 Polyhydroxystearate | 4.0 |
| PHASE B | |
| Water | 20.0 |
| PHASE C | |
| Dicaprylyl carbonate | 4.0 |
| Avobenzone | 3.0 |
| Octocrylene | 7.0 |
| Tinosorb ® S | 3.0 |
| Eusolex ® 6300 | 2.0 |
| PHASE D | |
| Cyclopentasiloxane | 2.0 |
| Farnesol (and) linalool | 0.5 |
| Tocopheryl acetate | 0.5 |
| PHASE E | |
| Water | 33.0 |
| Nanocapsules | 5.0 |
| Xanthan gum | 0.2 |
| EDTA disodium | 0.1 |
| Imidazolidinyl urea | 0.5 |
| Titanium dioxide | 1.0 |
| Tinosorb ® M | 2.5 |

1.2. Photoprotective Composition for the Body (SPF 45):

| Components | SPF 45 |
|---|---|
| PHASE A | |
| Acrylates/C10-30 alkyl acrylate crosspolymer | 0.05 |
| Triglycerides of caprylic/capric acid | 2.0 |
| Dimethicone | 2.0 |
| Isostearyl alcohol (and) butylene glycol cocoate (and) ethylcellulose | 4.5 |

-continued

| Components | SPF 45 |
|---|---|
| Ceteareth-20 | 1.5 |
| PEG-30 Polyhydroxystearate | 5.0 |
| PHASE B | |
| Water | 20.0 |
| PHASE C | |
| Dicaprylyl carbonate | 3.0 |
| Avobenzone | 3.0 |
| Octocrylene | 7.0 |
| Tinosorb S ® | 5.0 |
| Eusolex 6000 | 2.0 |
| PHASE D | |
| Cyclopentasiloxane | 2.0 |
| Farnesol, linalool | 0.5 |
| Tocopheryl acetate | 0.5 |
| PHASE E | |
| Water | 27.5 |
| Nanocapsules | 5.0 |
| EDTA disodium | 0.1 |
| Imidazolidinyl urea | 0.5 |
| Titanium dioxide | 1.0 |
| Tinosorb M | 5.0 |

Example 2

The particular composition of the invention as defined in Examples 1.1 and 1.2 were prepared as follows:

2.1. Preparation of the Nanocapsules:

The nanocapsules comprising octocrylene, avobenzone and buriti oil in the nucleus (denominated Nanophoton®) were prepared by interfacial polymer deposition.

The aqueous phase was prepared by dissolving 0.076 g polysorbate 80 (P80) in 53 mL of distilled water.

The organic phase was prepared by adding 0.076 g sorbitan monostearate, 0.100 g poly(ε-caprolactone), 0.125 g octocrylene, 0.025 g avobenzone and 0.125 g buriti oil, in 27 mL of acetone.

After dissolution of the components, the organic phase was added to the aqueous phase. The mixture was kept under agitation until complete homogenization and, afterwards, evaporated the acetone and water phase, concentrating the suspension to a final volume of 10 mL, adjusted in a volumetric flask.

A scheme for the preparation of the nanocapsules is shown in FIG. 1.

2.2. Preparation of the Semi-Solid Base:

The process for the preparation comprised the heating of phase A (80-90° C.), until the fusion of the components, and of phase B (80-90° C.). Phase B was added to phase A, under agitation. After cooling (50-60° C.), phase AB was added to phase C, with components already dissolved. The components of phase D were mixed and added to phase ABC, at room temperature. The components of phase E were dispersed in water and added to phase ABCD, under agitation, and mixed until complete homogenization.

2.3. Physico-Chemical Characterization of Nanocapsules:

Buriti oil has a red-orange color, and after the process of nanoprecipitation, the nanocapsules have a yellowish color.

Also, after the process of nanoprecipitation, the disagreeable odor of buriti oil was no longer perceivable.

2.4. Determination of Particle Size of the Nanocapsules:

An aliquot of 20 μL of the sample was diluted 500 times in a volumetric flask (10 mL), using as solvent MilliQ® water filtered with a Millipore® filter of 0.45 μm. Approximately 2 mL was transferred to analysis cuvettes (model ZEN0112), for measurement of the particle size, using a Zetasizer® nano-ZS model ZEN 3600 (Malvern, USA), with a laser source of 532 nm wavelength, and an angle measurement of 173°.

The average particle size of the nanocapsules was 237±7 nm, with a polydispersion of 0.19±0.02.

2.5. Determination of the Zeta Potential:

An aliquot of 20 µl of sample was diluted 500 times in a volumetric flask (10 mL), using, as solvent, solution of 10 mM NaCl in MilliQ® water filtered with a Millipore® filter of 0.45 µm. Approximately 1.5 mL was transferred to analysis cuvettes of model DTS1060, for measurement of zeta potential, using a Zetasizer® nano-ZS model ZEN 3600 (Malvern, USA), with a laser source of 532 nm wavelength, and an angle measurement of 173°.

Zeta potential is a measurement frequently utilized for surface characterization of nanoparticles, and provides a good approximation of the surface potential of the particles. In general, to obtain nanoparticles physically stable for long periods of time, the zeta potential should be different from zero. The potential of the nanocapsules was −11.5±1.3 mV, indicating stability to coalescence.

2.6. Measurement of the pH of the Nanocapsules:

pH was measured by adding the nanocapsules to a 15 mL beaker, and measuring pH with a Micronal B-474 pH meter, previously calibrated with Digimed® buffer solutions pH 4.00 and 6.02.

The measured pH for the nanocapsules was 6.01±0.1. The monitoring of the pH of the nanoparticles can provide important information, as, for example, indications of degradation of the polymer, relaxation of the polymeric chains and ionization of functional carboxylic groups, if present.

2.7. Measurement of Viscosity and Rheology:

Evaluation of the rheologic properties of the nanocapsules was realized with a Brookfield viscometer. The analysis was realized at 25° C.±1, using a bath with a heating element and circulation of water coupled to a thermostat. A ULA (Ultra Low Adapter) adapter and a spindle were also employed. The parameters for analysis were entered into the program Rheocalc V3.1-1. An initial velocity of 10 rotations per minute (rpm) was used, with 10 increases of 10 in 10 rpm, totalizing 20 points.

The viscosity of the nanocapsules was 3.2 Cp, at a rotation of 10 rpm. The rheological behavior exhibited by the nanocapsules was Newtonian behavior, that is, the viscosity remained constant with the variation of the shear rate.

Example 3

Photostability Studies of the Photoprotective Compositions.

Figure 2A:
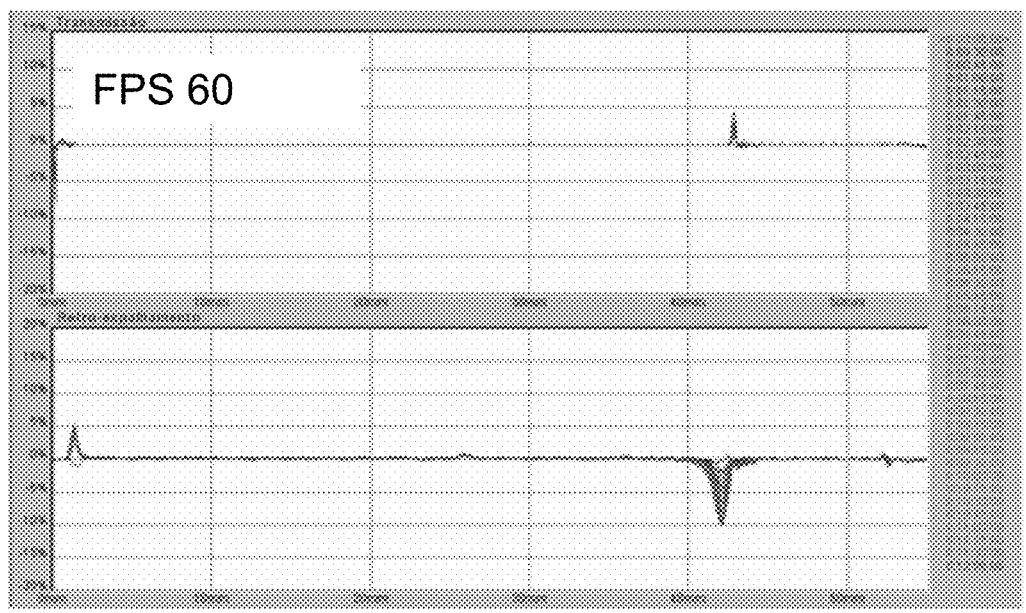
FIG. 2A presents a graphical analysis of the curves relative to 'transmission' and 'backscattering' of the fluid composition.
Figure 2B:
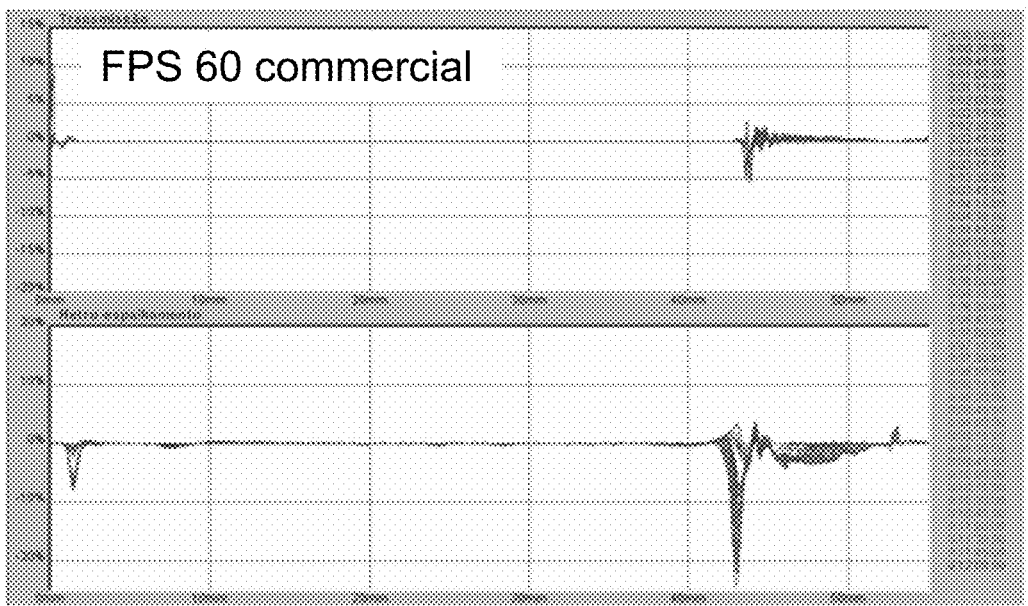
FIG. 2B presents a graphical analysis of the curves relative to 'transmission' and 'backscattering' of a commercial fluid composition, analyzed for 12 hours under the same conditions of analysis as the fluid composition of the invention.

3.1. Photostability Studies:

For the photostability studies, a volume of approximately 20 µL of semi-solid base was placed in quartz cuvettes, 10 mm, type 101-S (Suprazil). With the aid of a blade, a drop of semi-solid base was spread out so that it was sufficiently transparent (a few micrometers), permitting measurements of transmission and absorption. After 30 minutes, a reading was realized for the transmission and absorption in the UV (290 to 400 nm) at the initial time (t=0), using the spectrophotometer Varian Cary 50 UV-vis. After the initial reading, the cuvettes were irradiated with UVA radiation (300 to 400 nm, 90 Watts) and, at predetermined periods (2 in 2 hours), readings were realized for the transmission and absorption from 290 to 400 nm (FIGS. 2A and 2B). The absorption spectra of the times of irradiation were treated and the integral of the area of the absorption curve was calculated using the program Origin® 6.0.

The compositions used for the study were creams for the body (SPF 30) and fluids (SPF 45). These compositions were compared with existing compositions of the same line in the market, e.g. Sundown® Kids FPS (SPF) 30 (Johnson & Johnson) and Expertise® Kids Loção (Lotion) FPS 40 (L'Oreal).

Figure 3:
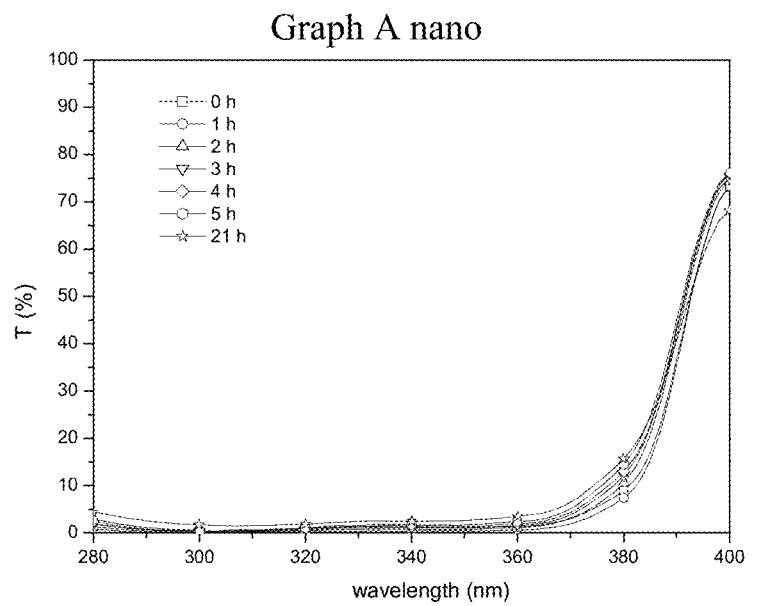
FIG. 3 presents transmission spectra after 21 hours of UVA irradiation (90 Watts): Graph A creme composition SPF 30; Graph B—Sundown@ Kids FPS 30 (Johnson & Johnson).
Figure 3:
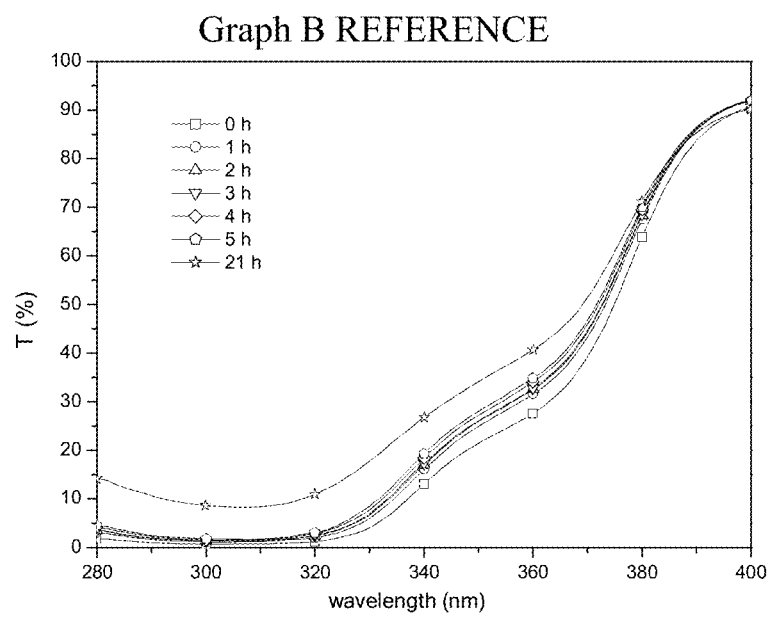

The photostability studies for the composition SPF 30 in comparison with the product Sundown® Kids FPS 30 (Johnson & Johnson) are demonstrated in FIG. 3. It shows that the transmission spectra presented by the composition SPF 30 (Graph A) blocked UV rays in the total required region of the spectra during 21 hours of exposure to UVA rays. The analysis demonstrated a critical wavelength ($\lambda_c$) near 380 nm and a UVA/UVB ratio of 0.81, values classified as superior UVA photoprotection.

The product Sundown® Kids FPS 30 (Johnson & Johnson) (Graph B), exhibited low protection in the UVA region, principally UVA 360 to 400 nm, and was not photostable after the 21 hours of irradiation.

The above results show the surprising and unexpected effect of the formulation of the present invention, including an improvement in the duration of the stability of the effect and its performance over broad spectra of radiation.

Figure 4:
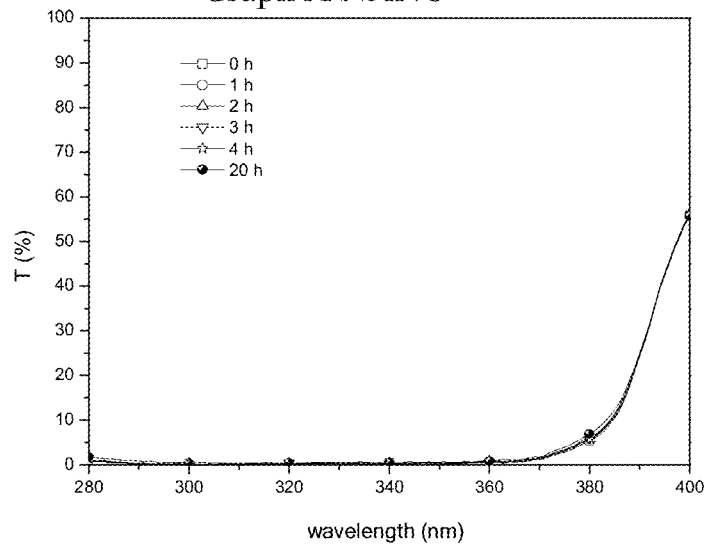
FIG. 4 presents transmission spectra after 20 hours of UVA irradiation (90 Watts): Graph A—fluid composition SPF 45 of the invention; Graph B—Expertise Kids Loção FPS 40 (L'Oreal).
Figure 4:
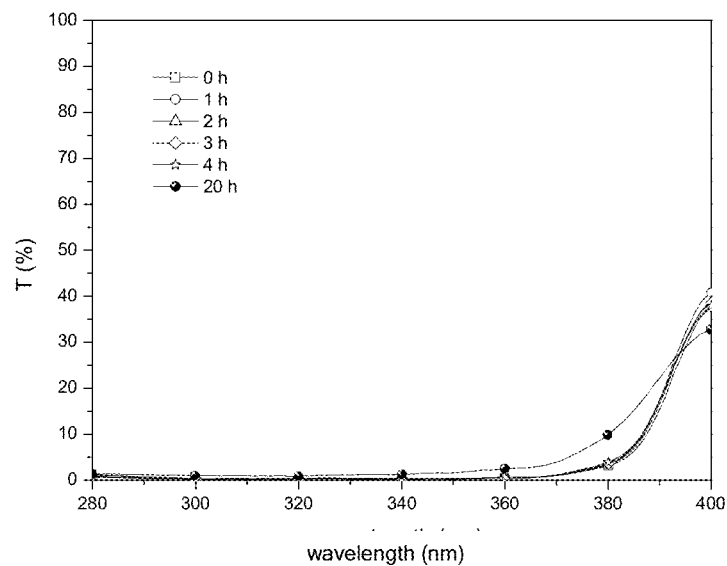

The spectra of the fluid composition SPF 45 of the invention, and of the composition Expertise® Kids Loção FPS 40 (L'Oreal), both containing avobenzone, are shown in FIG. 4. It shows the spectra of transmission of the fluid composition SPF 45 (Graph A) is photostable during 20 hours of UVA irradiation, maintaining the ability to block UVB and UVA rays during the experiment. Calculations demonstrate a $\lambda_c$ of 378 nm and a UVA/UVB ratio of 0.78, indicating good UVA protection. For Expertise® Kids Lotion FPS 40 (L'Oreal) (Graph B), good photoprotection was observed for total UVB and UVA spectra during the 20 hours of analysis under UVA radiation.

Example 4

To experimentally verify the effect of encapsulation of oil and UV filter on the photostability of the photoprotective compositions of the present invention, the following formulations were prepared, as described in Examples 1 and 2: formulation Lotion (including filter and buriti oil—neither encapsulated), formulation Lotion NC (including Nanophoton®—filter and buriti oil co-encapsulated.

Figure 5:
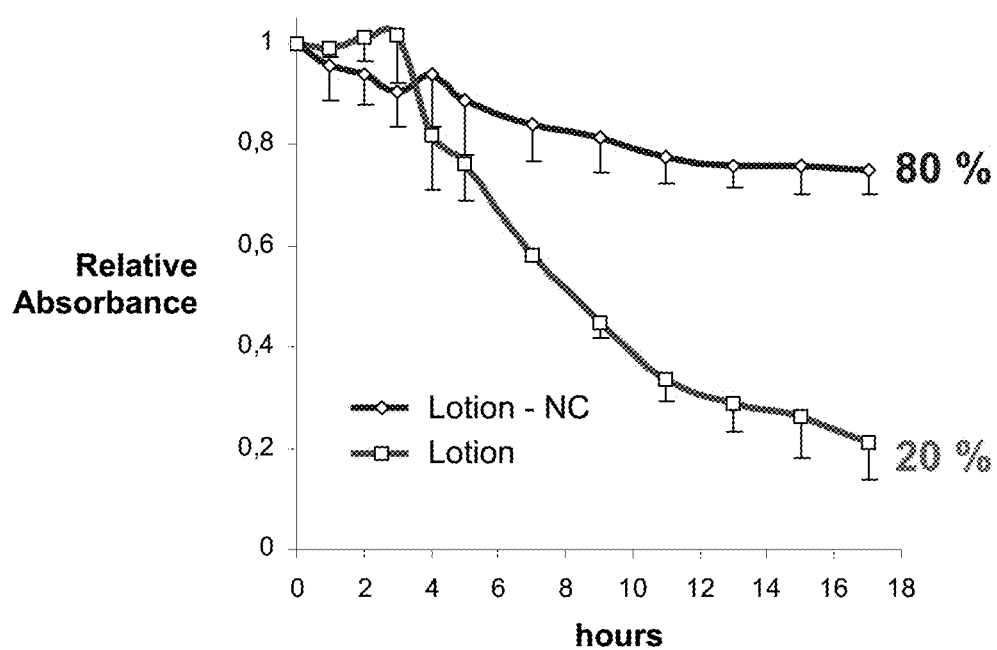
FIG. 5 presents side-by-side results of the photostability of a lotion composition without the nanocapsules (Lotion) and a lotion composition with the nanocapsules comprising filter and buriti oil (Lotion-NC), after UVA irradiation (90W).

The comparative results of photostability, after UVA irradiation (90 W), between the formulations Lotion (filter and oil not nanoencapsulated) and Lotion NC (filter and oil co-nanoencapsulated) showed a positive effect of the nanoencapsulation on the stability of the formulation as to UVA absorption (FIG. 5).

The invention claimed is:

1. Polymeric nanocapsules having a core consisting of components:
   (a) buriti oil;
   (b) octocrylene and avobenzone UV filters; and
   (c) sorbitan monostearate;
   wherein the core is encapsulated by poly(ε-caprolactone) and polysorbate 80 and the polymeric nanocapsules have a particle size in a range of 230 nm to 244 nm.

2. The polymeric nanocapsules of claim 1, wherein the nanocapsules comprise from 0.001% to 50% by weight of the total weight of the polymeric nanocapsules of buriti oil.

3. The polymeric nanocapsules of claim 1, wherein the nanocapsules comprise from 0.001% to 50% by weight of the total weight of the polymeric nanocapsules of octocrylene and avobenzone UV filter.

4. The polymeric nanocapsules of claim 1, wherein the nanocapsules comprise from 0.0001% to 50% by weight of the total weight of the polymeric nanocapsules of poly($\varepsilon$-caprolactone) polymer and polysorbate 80.

5. The polymeric nanocapsules of claim 1, wherein the nanocapsules comprise from 0.0001% to 50% by weight of the total weight of the polymeric nanocapsules of sorbitan monostearate.

6. A method for preparing a photoprotective composition, wherein the method comprises combining the polymeric nanocapsules of claim 1 with one more physiologically acceptable excipients or cosmetic auxiliaries.

* * * * *